(12) United States Patent
Boyd et al.

(10) Patent No.: US 9,504,857 B2
(45) Date of Patent: Nov. 29, 2016

(54) ORAL CARE FORMULATIONS FOR MALODOR CONTROL

(75) Inventors: Thomas Boyd, Metuchen, NJ (US); Leonora Leigh, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 355 days.

(21) Appl. No.: 13/522,563

(22) PCT Filed: Jan. 28, 2011

(86) PCT No.: PCT/US2011/022864
§ 371 (c)(1),
(2), (4) Date: Jul. 17, 2012

(87) PCT Pub. No.: WO2011/094497
PCT Pub. Date: Aug. 4, 2011

(65) Prior Publication Data
US 2012/0288548 A1 Nov. 15, 2012

Related U.S. Application Data

(60) Provisional application No. 61/299,764, filed on Jan. 29, 2010.

(51) Int. Cl.
| | | |
|---|---|---|
| *A61Q 11/00* | (2006.01) | |
| *A61K 8/02* | (2006.01) | |
| *A61K 8/27* | (2006.01) | |
| *A61K 8/73* | (2006.01) | |
| *A61K 8/81* | (2006.01) | |

(52) U.S. Cl.
CPC ............ *A61Q 11/00* (2013.01); *A61K 8/0216* (2013.01); *A61K 8/0233* (2013.01); *A61K 8/27* (2013.01); *A61K 8/731* (2013.01); *A61K 8/736* (2013.01); *A61K 8/8152* (2013.01); *A61K 8/8182* (2013.01)

(58) Field of Classification Search
CPC .... A61K 8/0216; A61K 8/0233; A61K 8/27; A61K 8/731; A61K 8/736; A61K 8/8152; A61Q 11/00
USPC .................................................... 424/401, 49
See application file for complete search history.

(56) References Cited

U.S. PATENT DOCUMENTS

| | | |
|---|---|---|
| 4,187,287 A | 2/1980 | Schreiber et al. |
| 4,820,506 A | 4/1989 | Kleinberg et al. |

(Continued)

FOREIGN PATENT DOCUMENTS

| | | |
|---|---|---|
| CA | 2670524 | 6/2008 |
| JP | H02-059513 | 2/1990 |

(Continued)

OTHER PUBLICATIONS

International Search Report and Written Opinion in International Application No. PCT/US11/022864, mailed Apr. 2, 2013.

(Continued)

*Primary Examiner* — Anna Pagonakis
*Assistant Examiner* — Miriam A Levin

(57) ABSTRACT

Described herein are oral care compositions comprising an orally acceptable carrier; and a film, wherein said film comprises an odor controlling active; a mucoadhesive polymer; a release-rate modulating polymer; a polymeric base; and optionally a flavorant; and wherein said film controls release of said odor controlling active.

8 Claims, 2 Drawing Sheets

(56) References Cited

U.S. PATENT DOCUMENTS

| | | | |
|---|---|---|---|
| 4,839,157 A | 6/1989 | Mei-King Ng et al. | |
| 4,900,552 A | 2/1990 | Sanvordeker et al. | |
| 5,032,384 A * | 7/1991 | Yeh et al. | 424/49 |
| 5,047,244 A | 9/1991 | Sanvordeker et al. | |
| 5,695,746 A | 12/1997 | Garlick, Jr. et al. | |
| 5,700,478 A | 12/1997 | Biegajski et al. | |
| 5,738,840 A | 4/1998 | Richter | |
| 5,948,430 A | 9/1999 | Zerbe et al. | |
| 6,159,447 A | 12/2000 | Budny et al. | |
| 6,241,974 B1 | 6/2001 | White, Jr. et al. | |
| 6,284,264 B1 | 9/2001 | Zerbe et al. | |
| 6,315,986 B1 | 11/2001 | Wong et al. | |
| 6,379,652 B1 * | 4/2002 | Liu et al. | 424/49 |
| 6,403,536 B1 * | 6/2002 | Forsythe et al. | 504/357 |
| 6,419,903 B1 | 7/2002 | Xu et al. | |
| 6,514,483 B2 | 2/2003 | Xu et al. | |
| 6,585,997 B2 | 7/2003 | Moro et al. | |
| 6,592,887 B2 | 7/2003 | Zerbe et al. | |
| 6,596,298 B2 | 7/2003 | Leung et al. | |
| 6,664,254 B1 | 12/2003 | Rogozinski | |
| 6,669,929 B1 | 12/2003 | Boyd et al. | |
| 6,723,305 B2 | 4/2004 | DePierro et al. | |
| 6,748,779 B2 | 6/2004 | Allart | |
| 7,132,113 B2 | 11/2006 | Zerbe et al. | |
| 7,250,162 B2 | 7/2007 | Oh | |
| 7,297,327 B2 | 11/2007 | Pilch et al. | |
| 7,402,416 B2 | 7/2008 | Szeles et al. | |
| 2003/0158111 A1 | 8/2003 | Bar-Or | |
| 2004/0115137 A1 | 6/2004 | Verrall et al. | |
| 2004/0156794 A1 | 8/2004 | Barkalow et al. | |
| 2004/0202698 A1 | 10/2004 | Ramji et al. | |
| 2005/0118217 A1 | 6/2005 | Barnhart et al. | |
| 2006/0008425 A1 | 1/2006 | Masters et al. | |
| 2006/0045660 A1 | 3/2006 | Di Rosa | |
| 2006/0073174 A1 | 4/2006 | Moro et al. | |
| 2008/0152600 A1 | 6/2008 | Huang et al. | |
| 2008/0254079 A1 | 10/2008 | Ferrari | |
| 2012/0020899 A1 * | 1/2012 | Zaidel et al. | 424/52 |

FOREIGN PATENT DOCUMENTS

| | | |
|---|---|---|
| JP | H03-258724 | 11/1991 |
| JP | 2001-163745 | 6/2001 |
| WO | WO 00/18365 | 4/2000 |
| WO | WO 00/59423 | 10/2000 |
| WO | WO 2004/060335 | 7/2004 |
| WO | WO 2005/039499 | 5/2005 |
| WO | WO 2005/058265 | 6/2005 |
| WO | WO 2005/092271 | 10/2005 |
| WO | WO 2006/009737 | 1/2006 |
| WO | WO 2010/138544 | 12/2010 |
| WO | WO 2012/002945 | 1/2012 |
| WO | WO 2012/002946 | 1/2012 |

OTHER PUBLICATIONS

Sterer et al., 2008, "Oral malodor reduction by a palatal mucoadhesive tablet containing herbal formulation," J. Dentistry 36(7):535-539.

* cited by examiner

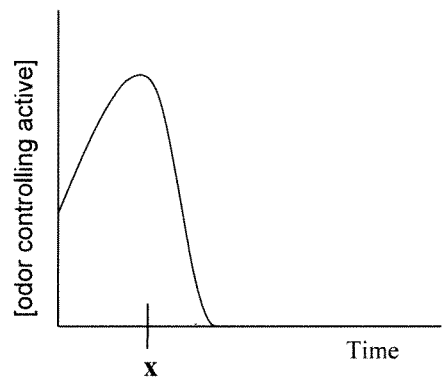
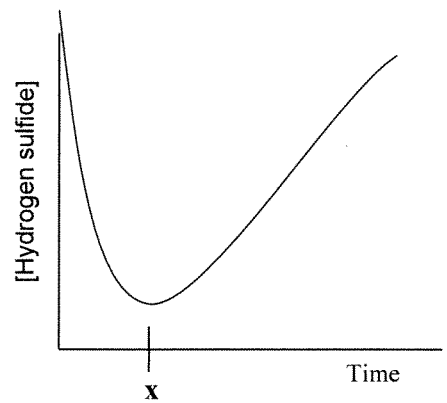
FIGURE 1(a)  FIGURE 1(b)
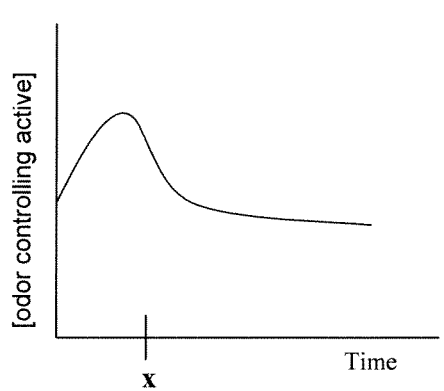
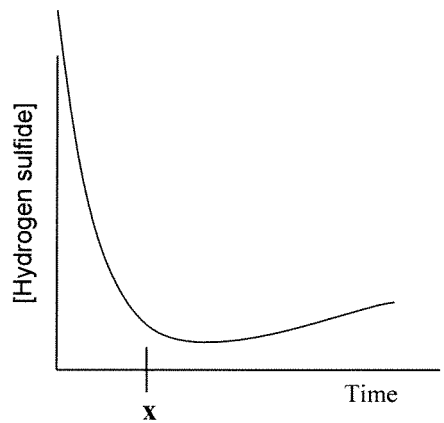
FIGURE 2(a)  FIGURE 2(b)

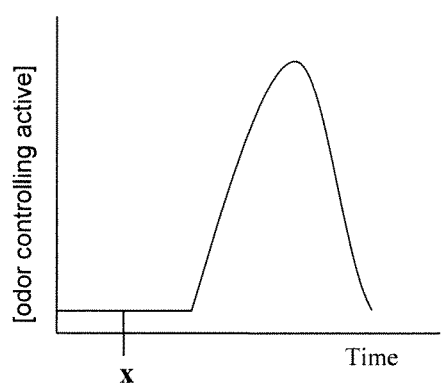 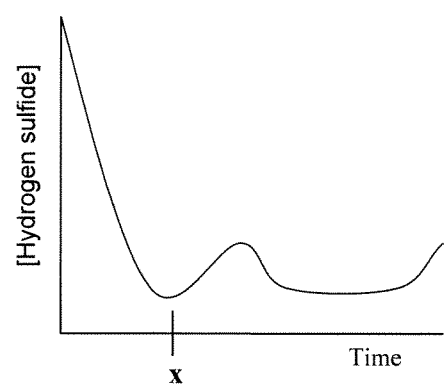
FIGURE 3(a)                    FIGURE 3(b)

ORAL CARE FORMULATIONS FOR MALODOR CONTROL

CROSS-REFERENCE TO RELATED APPLICATIONS

This application is a national stage entry under 35 U.S.C. §371 of International Patent Application No. PCT/US2011/022864, filed Jan. 28, 2011, which claims priority to U.S. Provisional Patent Application No. 61/299,764, filed Jan. 29, 2010, which is are incorporated herein by reference.

BACKGROUND

Halitosis, the technical term for bad breath or malodor is considered one of the most common and sometimes debilitating problems that can cause embarrassment and affect the quality of life. Often people suffering from bad breath remain unaware of it. Oral malodor is produced by overgrowth of oral microorganisms that produce volatile sulfur compounds ("VSC") namely hydrogen sulphide, methylmercaptan and dimethyl sulphide. The treatment is aimed at the reduction of microorganisms in the oral cavity, neutralizing of the VSC compounds or masking the bad odors. The challenges in accomplishing this goal have been poor delivery and retention of the odor control molecules in the oral cavity. Most often, actives do not reach the target site partly because they are easily rinsed away and also they do not bind to the tooth or mucosal surfaces. The actives are therefore not retained for long periods and this greatly impairs their ability to exert their action.

The aesthetic appeal of compositions for malodor control is important, and can have significant effects on consumer acceptance and usage. Aesthetic effects have been acknowledged to play an important role in consumer acceptance of many products. Although such products have met with consumer approval, the art seeks to further improve the aesthetic effects as well as the cosmetic and therapeutic benefits of these products. Indeed, many such compositions known in the art are deficient in one or more attributes.

Although some commercially available products have met with consumer approval, many do not control halitosis or malodor effectively because the odor controlling actives are easily washed away and are therefore not retained for long periods of time in the oral cavity. Accordingly, there is still a need for products that allow odor controlling actives to stay resident in the oral cavity for extended periods of time, and reduce or eliminate bad breath or malodor.

SUMMARY

Some embodiments of the present invention provide compositions capable of providing extended, delayed or controlled release of an odor controlling active. In some embodiments, the odor controlling active binds to teeth or oral cavity mucosa. In some embodiments, the odor controlling active entraps volatile sulfur compounds and other products that cause bad breath.

Some embodiments of the present invention provide an oral care composition comprising an orally acceptable carrier; and a film comprising: an odor controlling active; a mucoadhesive polymer; a release modulating polymer; a polymeric base; and an optional flavorant. In some embodiments, the film controls release of said odor controlling active. In some embodiments, the odor controlling active is released at a rate which provides exposure of the odor controlling active to the oral cavity over an extended period of time.

In some embodiments, the film comprises a plurality of film fragments. In other embodiments, the present invention provides a composition comprising a plurality of lamellar fragments in a carrier.

In some embodiments, the oral care composition includes a multilayer film entrained in an orally acceptable vehicle, the multilayer film containing at least one mucoadhesive layer and one overlying layer, the mucoadhesive layer including a mucoadhesive polymer, a first polymeric base and an odor controlling active and the overlying layer including a release modulating polymer, a second polymeric base and optionally a flavorant.

Some embodiments of the present invention provide a method for treating or preventing malodor comprising: administering to subject in need thereof, an oral care composition comprising a film for extended or delayed release of an odor controlling active, wherein the film comprises a mucoadhesive polymer, a release modulating polymer, a polymeric base, and an odor controlling active.

In another embodiment, the invention provides a method of preparing oral care compositions including a mucoadhesive film entrained in a controlled release carrier, wherein the film has an odor controlling active which includes:

a. providing an orally acceptable carrier;
b. adding a multilayer film containing at least one mucoadhesive layer and one overlying layer, the mucoadhesive layer including a mucoadhesive polymer, a first polymeric base and an odor controlling active and the overlying layer including a release modulating polymer, a second polymeric base and a flavorant in an amount from about 35% by weight to about 60% by weight to the carrier to form a mixture; and
c. homogenizing the mixture.

BRIEF DESCRIPTION OF THE DRAWINGS

In FIGS. 1(a)-3(a), time "x" indicates the end of brushing time, followed immediately by expectoration, and by most users, by quick rinsing with 10-15 mL of additional water.

FIG. 1(a) depicts a graph illustrating the concentration of odor controlling active present in the oral cavity during and after brushing with a conventional composition.

FIG. 1(b) depicts a graph illustrating the hydrogen sulfide concentration of the oral cavity, during and after brushing with a conventional composition.

FIG. 2(a) depicts a graph illustrating the concentration of odor controlling active present in the oral cavity during and after brushing with a composition of the present invention.

FIG. 2(b) depicts a graph illustrating the hydrogen sulfide concentration present in the oral cavity, during and after brushing with a monolayer film composition of the present invention.

FIG. 3(a) depicts a graph illustrating the effect of the controlled release of an odor controlling active from a two-layer film embodiment of the present invention FIG. 3(b) depicts a graph illustrating the hydrogen sulfide concentration present in the oral cavity, during and after brushing with a multi-layer film composition of the present invention.

DETAILED DESCRIPTION

As referred to herein, an "oral care composition" as used herein is meant a composition for which the intended use can include oral care, oral hygiene, or oral appearance, or for which the intended method of use can comprise administration to the oral cavity.

As used herein, a "release modulating polymer" refers to a polymer material suitable for use in oral care formulations that retards the release of an odor controlling active, or other active agent, from the films and/or compositions described herein. Examples of suitable release modulating polymers can be found in Remington's Pharmaceutical Sciences, 18$^{th}$ Ed., Gennaro, ed., Mack Publishing Co., Easton, Pa., 1990), the contents of which are hereby incorporated by reference in its entirety.

Some embodiments of the present invention provide an oral care composition comprising: an orally acceptable carrier; and a film comprising: an odor controlling active; a mucoadhesive polymer; a release modulating polymer; a polymeric base; and optionally a flavorant; wherein said film controls release of said odor controlling active. In some embodiments, the odor controlling active is selected from the group consisting of: an odor eliminating compound; an odor adsorbing compound; and an odor blocking compound. In some embodiments, the odor eliminating compound is a zinc containing compound selected from the group consisting of: zinc oxide, zinc citrate, zinc lactate, zinc chlorite, zinc chloride, zinc zeolite, and a combination of two or more thereof.

In some embodiments, the mucoadhesive polymer is selected from the group consisting of: a polyacrylic acid or polyacrylate, a cross-linked polyacrylic acid or polyacrylate, a polyalkyl acrylate, a cross-linked polyalkyl acrylate, polyvinylpyrrolidone, a copolymer of polyvinylpyrrolidone and polyacrylate, chitosan or chemically-modified chitosan, and or a combination of two or more thereof.

In some embodiments, the release modulating polymer is polyvinyl acetate or hydroxylethyl cellulose. In some embodiments, the release modulating polymer is polyvinyl acetate.

In some embodiments, the polymeric base is selected from the group consisting of: hydroxypropylmethyl cellulose, methyl cellulose, hydroxypropyl cellulose and copolymers thereof.

Some embodiments of the present invention provide oral care compositions comprising a film, wherein the film comprises: a mucoadhesive polymer; a release modulating polymer; a polymeric base; an odor controlling active; and optionally a flavorant. In some embodiments, the mucoadhesive polymer comprises from about 2% to about 4% by weight of the film. In some embodiments, the release modulating polymer comprises from about 5% to about 30% by weight of the film. In some embodiments, the release modulating polymer comprises from about 5% to about 10% by weight of the film. In other embodiments, the release modulating polymer comprises from about 20% to about 30% by weight of the film. In further embodiments, the polymeric base comprises from about 30% to about 50% by weight of the film. In yet other embodiments, the odor controlling active comprises from about 40% to about 50% by weight of the film.

In some embodiments, the oral care composition comprises a film, wherein the film comprises: a mucoadhesive polymer comprising from about 2% to about 4% by weight of the film; a release modulating polymer comprising from about 5% to about 30% by weight of the film; a polymeric base comprising from about 30% to about 50% by weight of the film; and an odor controlling active comprising from about 40% to about 50% by weight of the film. In some embodiments, the film comprises from about 0.5% to about 50% by weight of the oral care composition. In some embodiments, the film comprises from about 5% to about 35% by weight of the oral care composition. In some embodiments, the film comprises from about 15% to about 20% by weight of the oral care composition. In other embodiments, the multilayer film comprises from about 0.5% to about 50% by weight of the oral care composition. In other embodiments, the multilayer film comprises from about 5% to about 35% by weight of the oral care composition. In other embodiments, the multilayer film comprises from about 15% to about 20% by weight of the oral care composition.

Some embodiments, of the present invention provide an oral care composition comprising: a multilayer film entrained in an orally acceptable vehicle, the multilayer film comprising at least one mucoadhesive layer and one overlying layer, the mucoadhesive layer comprising a mucoadhesive polymer, a first polymeric base and an odor controlling active and the overlying layer comprising a release modulating polymer, a second polymeric base and a flavorant.

In some embodiments, the mucoadhesive polymer comprises from about 2% to about 4% by weight of the mucoadhesive layer. In further embodiments, the one or more release modulating polymers comprise from about 5% to about 10% by weight of the overlying layer. In other embodiments, the one or more release modulating polymers comprise from about 20% to about 30% by weight of the overlying layer. Yet further embodiments provide a composition wherein the first polymeric base comprises from about 30% to about 50% by weight of the multilayer film. Further embodiments provide a composition wherein the second polymeric base comprises from about 30% to about 50% by weight of the multilayer film. Still further embodiments provide a composition wherein the odor controlling active comprises from about 40% to about 50% by weight of the mucoadhesive layer.

Further embodiments of the present invention provide a method for treating or preventing malodor comprising: administering to subject in need thereof, an oral care composition comprising a film for extended or delayed release of an odor controlling active, wherein the film comprises: a mucoadhesive polymer, a release modulating polymer, a polymeric base, and an odor controlling active. In some embodiments, the film is a multilayer film comprising at least one mucoadhesive layer and one overlying layer, the mucoadhesive layer comprising: a mucoadhesive polymer, a first polymeric base and an odor controlling active; and the overlying layer comprising: a release modulating polymer, a second polymeric base, and optionally a flavorant.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The oral care compositions of the various embodiments preferably are in the form of a dentifrice. The term "dentifrice" as used throughout this description, denotes a paste, gel, lozenge, gum, or liquid formulation. The dentifrice may be in any desired form, such as deep striped, surface striped, multi-layered, having a gel surround the paste, or any combinations thereof. The film contained in the oral care composition may be of any desired shape or structure, including multiple small strips, or one continuous strip.

The expressions "carrier" or "aqueous cattier" as used throughout this description denote any safe and effective materials for use herein. Such materials include, for example, thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

All percentages and ratios used herein are by weight of the oral care composition, unless otherwise specified. All measurements are made at 25° C., unless otherwise specified. The recitation of a specific value herein, whether referring to respective amounts of components, or other features of the embodiments, is intended to denote that value, plus or minus a degree of variability to account for errors in measurements. For example, an amount of 10% may include 9.5% or 10.5%, given the degree of error in measurement that will be appreciated and understood by those having ordinary skill in the art.

Films

As used herein, a "film" refers to a material having a substantially lamellar structure. A "lamellar" structure has, or is capable of having, a size in one or two dimensions (e.g., the x- or y-dimensions) that is substantially greater than the thickness of the structure in a third dimension (e.g., the z-direction). Lamellar structures among those useful herein include those that are substantially planar, layered, or lamelliform. In one embodiment, the lamellar structure is substantially planar, having a size in both the x- and y-dimensions that is substantially greater than the z-direction. In other embodiments, the lamellar structure is non-planar. In one embodiment, a film of this invention comprises a substantially continuous surface that can appear as a substantially flat surface, although in some embodiments the film may be deformed. In such embodiments, the film can have any of a number of shapes, including having a smooth curved surface. The fragments may be of a desired size and may be of regular or irregular perimeter.

Some embodiments of the present invention comprise a film for delayed or extended release of an odor controlling active. Binding of the films to the surface of the teeth and/or mucosa of the oral cavity enables longer retention of bactericidal actives to bacterial cells, thereby killing the bacteria that produce volatile sulfur compounds. Additionally, the presence of different layers in the film would provide a larger surface area thereby ensuring delivery of high concentrations of odor controlling actives to target sites.

As used herein, the terms "instant release" or "instant release composition" refer to compositions that provide a rapid and non-gradual release of active from the composition. Such instant release compositions are either devoid of release modulating polymers or other species that retard the release of the active compound from the composition, or contain such polymers or species in amounts that are sufficiently small such that the release of the active from the compound is not retarded relative to an otherwise identical formulation lacking such polymers or species.

As used herein the terms "controlled release", "controlled release oral care composition", and the like, refer to oral care compositions that contain materials that retard the release of an active from the composition relative to an "instant release" composition as described above. Thus, the term "controlled release" can apply to any number of extended release forms and will be considered substantially synonymous with delayed release, time release, prolonged release, time programmed release, time released, time coated release, sustained release, slow acting, long acting, delayed acting, spaced release, time spaced release, extended acting, extended release, extended action, and the like.

As used herein, an "odor controlling active" or "active" refers to all functional compounds which are preferably delivered via oral cavity either from a toothpaste or rinse formulation and which can be utilized in three main areas of odor control, namely by odor elimination, odor adsorption and odor blocking.

Odor controlling actives suitable for odor elimination include but are not limited to zinc containing compounds such as zinc oxide, zinc citrate and zinc zeolite as more particularly described in U.S. Patent Publication No. 2006/0045860. In addition, other metal-containing compounds, such as those of copper, stannous, bismuth, strontium; succulents or other ingredients which increase salivary flow, act to wash away odors; and thus, are useful in the compositions described herein. Certain strong citrus-based flavorants; odor absorption complexes, which entrap or adsorb malodor molecules, such as for example, Ordenone® as manufactured by Bell Air Fragrances, Inc. are also useful in the claimed compositions. Ordenone® has the ability to encapsulate malodor molecules such as mercaptans, sulfides and amines within its structure, as disclosed in, for example, U.S. Pat. No. 6,664,254.

Odor controlling actives suitable for odor blocking or as odor blockers, include but are not limited to enzymes that can interrupt the process by which odors are created. For example, odor blocking enzymes such as arginine deiminase, can be effectively formulated within mucoadhesive films. Also, molecules that effectively inhibit the bacterial production of malodor molecules can be used to control odor, for example agents that interfere with the bacterial enzymes cysteine desulfhydrase and/or methionine γ-lyase.

Odor controlling actives suitable for odor blocking or as odor blockers, include but are not limited to agents that act by oxidizing or otherwise chemically reacting with malodor molecules, including peroxides, perchlorites, and reactive molecules with activated double bonds.

As used herein, the term "mucoadhesive" refers to hydrophilic polymers, natural or synthetic, which by the hydrophilic designation, can be either water soluble or swellable and which are adhesive to mucosal surfaces. Preferably such adhesives adhere the odor controlling active containing formulation to the mucosal tissues and/or teeth as well as functioning as a reservoir of this and other active substances which can be dissolved or absorbed via contacting the mucosal membrane.

Mucoadhesive polymers useful for this invention include without limitation carboxy polymethylene commercially available as Carbopol® CP94ONF, CP971NF, CP974PNF, polyvinyl pyrrolidone ("PVP") commercially available as Plasdone K-90 USP, and Polycarbophil® available commercially as Noveon AA-1 USP (PC), hydroxypropyl cellulose, sodium carboxymethyl cellulose, hydroxypropyl methyl cellulose, hydroxyethyl cellulose, polyvinyl alcohol, poly (isobutylene), poly(isoprene), poly(acrylic acid), natural gums, such as xanthan and locust bean gum, chitosan and chemical derivatives of chitosan, pectin, silicones, and mixtures and co-polymers of these.

Carbopol® 940 polymer is a cross-linked polyacrylate polymer known as a bioadhesive and also highly efficient rheology modifier capable of providing high viscosity to a composition. Policarbophils are polymers of acrylic acid cross linked with divinyl glycol useful as bioadhesives and also in designing controlled-release formulations.

Preferably the mucoadhesive polymer comprises from about 0.5% to about 20% by weight of the film, preferably from about 1% to about 10% by weight, and more preferably from about 2% to about 4% by weight.

In some embodiments, the film comprises a polymeric base. In some embodiments, the polymeric base is selected from a water soluble polymer such as hydroxypropylmethyl cellulose, methyl cellulose, hydroxypropyl cellulose and mixtures of copolymers thereof. In other embodiments, film-forming polymers such as polyvinyl alcohol, polyvinylpyrrolidone and the like, may be used.

As a result of the present invention, oral care formulations are provided including orally acceptable carriers and mucoadhesive, water erodible mono or multilayer films that release odor controlling actives in an extended or prolonged manner and are removable from the oral cavity by the constant flow of saliva. As used herein, "water erodible" means a material or substance that does not dissolve in water or saliva in total, however will disintegrate and completely break apart upon exposure to water or saliva.

While monolayer and multilayer films will be described with more particularity below, the release rate of the odor control active from such films is determined by the rate at which these films dissolve or disperse in the fluid environment of the oral cavity, and by the diffusion rate at which the odor controlling active is released from within the film. The release rate of the odor control active from the film matrix can be easily tailored to provide a range from minutes to hours as desired by adjusting the amount of the release modulating polymer and/or the polymeric base in the film matrix. For example, increasing the amount of polyvinyl acetate can reduce film swelling but increase the retention time of the film on the oral cavity mucosa and teeth thereby delaying the release of the odor controlling active from the film.

In one preferred embodiment, the release modulating polymer present in the films of this invention varies from 0.1% to 30% and more preferably from 0.5% to 20% and most preferably from 5% to 20%. Further, the amount of polymeric base preferably varies from 5% to 80% more preferably from 10% to 60% and most preferably from 40% to 50%.

Adjusting the content of the odor controlling active present in the films of the invention can also be used to control, extend or delay the release of the odor controlling active. Ideally, the level of odor control active is as high as possible. However, practically, one must balance activity with the ability to manufacture and handle the final film. Therefore, preferably, the amount of the odor controlling active varies from 10% to 70%, preferably from 10% to 60%, and more preferably from 40% to 60%. In some embodiments, the odor controlling active comprises from about 15% to about 25% by weight of the film.

Methods of Preparing Films

The extended or delayed release films of the present invention can be prepared using methods known in the art such as conventional extrusion, aqueous and solvent casting processes.

In some embodiments a single layer film comprising a mucoadhesive polymer, a release modulating polymer, a polymeric base and an odor controlling active is provided. In preparing the monolayer film according to the present invention the mucoadhesive polymer, the release modulating polymer, the polymer base, an odor controlling active and optionally a colorant, flavorant, sweetener and/or therapeutic agents and other film forming ingredients are dissolved in a compatible solvent to form a film forming composition.

Examples of suitable solvents include water, alcohols, acetone, ethyl acetate or mixtures thereof. After a solution has been formed, a plasticizer can be added with stirring, and heat is applied if necessary to aid dissolution, until a clear and homogeneous solution has been formed. The solution can be coated onto a suitable carrier material and dried to form a film. The carrier material should have a surface tension which allows the film solution to spread evenly across the intended carrier width without soaking to form a destructive bond between the film carrier substrates. Examples of suitable carrier materials include glass, stainless steel, teflon and polyethylene-impregnated paper. Drying of the film may be carried out at high temperature using a drying oven, drying terminal, vacuum drier, or any other suitable drying equipment which does not adversely effect the ingredients of which the film is composed.

In some embodiments, the film thickness ranges from 0.5 to 10 mils (1 mil=0.001 inches), preferably from 1 to 5 mils, more preferably from 1.5 to 2.5 mils for a single layer film and from 2 to 4 mils for a double or triple layer film. In some embodiments, the dried film is cut or punched into shaped flakes having a particle size of 0.01 to 0.50 inches, preferably 0.08 to 0.25 inches.

Additional stability can be provided to the shapes formed from the dried film, by applying to the film, before shaping into flakes, a protective barrier overcoat such as food grade shellac or ethyl cellulose.

When the film is to be used for decorative effect, the film once formed is cut or punched into various attractive shaped flakes such as hearts, stars, diamonds and circles. In some embodiments, the film flakes are incorporated in the base dentifrice of the present invention at a concentration of 0.05% to 1.0% by weight, preferably 0.1% to 0.5% by weight. In some embodiments a first film is used for decorative effect at a lower concentration, and another film is made transparent or otherwise un-noticeable at a higher concentration.

In some embodiments a two-layer film is provided. The two layer film can be formed by successively forming the layers (A and B) by casting from a respective slurry and subsequent drying for each layer. For example, the first layer ("A") can be cast from a slurry composition including a mucoadhesive polymer, a first polymeric base and an odor controlling active as a 0.010 inch layer, and then dried for 10 minutes in an oven at a temperature of 100° C. The second layer ("B") can then be cast over the first layer from a slurry composition including a release modulating polymer, a second polymeric base and a flavorant as a 0.020 inch layer, and then dried for 10 minutes in the oven at 100° C. The presence of a layer containing a release modulating polymer and/or other release modulating compound is believed to contribute to delaying or extending the release of the odor controlling active from the mucoadhesive containing layer. As a result of incorporating the films of this invention in a dentifrice or mouth rinse, the consumer can use oral care formulations that can deliver odor controlling actives to target sites and/or hard to reach areas in the oral cavity. In some embodiments, selective binding onto the saliva coated surface of the oral cavity by the Carbopol® containing layer of the film occurs. In some embodiments, the polyvinyl acetate containing layer of the two layer film does not adhere to the oral cavity mucosa or teeth surface, but instead delays and/or prolongs the release of the odor controlling active.

Consequently, the two layer film tends to stick to the inside portion or soft palate of the oral cavity and erodes slowly at the release modulator including layer but more rapidly at the mucoadhesive polymer including layer, resulting in the prolonged and/or delayed release of the odor controlling active.

Some embodiments provide a three layer film. The three layer film can be formed by successively forming the layers (C, D and C') by casting from a respective slurry and subsequent drying for each layer. For example, the first layer ("C") can be cast from a slurry composition including a mucoadhesive polymer, a first polymeric base and an odor controlling active as a 0.010 inch layer, and then dried for 10 minutes in an oven at a temperature of 100° C. Then, the second layer ("D") can be cast over the second layer from a slurry composition including a release modulating polymer, a second polymeric base and a flavorant as a 0.020 inch layer, and then dried for 10° C., minutes in the oven at 100° C. Finally, the third layer ("C'") can be cast over the second layer from a slurry composition including a mucoadhesive polymer, a first polymeric base and an odor controlling active as a 0.010 inch layer, and then dried for 10 minutes in an oven at a temperature of 100° C. Films can be made sequentially, such as illustrated above, or formed as a multi-layer laminar slurry directly from the component slurries. The laminar slurry would then be dried in a similar manner. Combinations of methods are also possible. For example, extrusion of layers can be followed by solvent casting of different layers.

In some embodiments, the present invention provides a three-layer film wherein the outer surface layers are water erodible and include a mucoadhesive polymer, a first polymeric base and a release-modulating polymer, while the center layer incorporates a flavorant, an odor controlling active and a second polymeric base.

The overall benefits provided by the mucoadhesive films of the present invention are also illustrated in FIGS. 1-3.

FIG. 1 illustrates control of malodor as a function of time using odor control compositions available in the prior art, such as toothpaste or mouthwash. As shown in FIG. 1a, once the odor controlling active is released during use, such as during brushing, it is quickly rinsed away by normal saliva flow and the levels of volatile sulfur compounds such as hydrogen sulfide quickly rise once the brushing is completed. (See, FIG. 1(b)). FIG. 1(a) demonstrates that upon completion of brushing at time "x", the odor controlling active is rapidly cleared from the oral cavity by salivary flow. As shown in FIG. 1(b), the odor controlling active is not present for a substantial period of time post-brushing, which allows the odor-causing bacteria to rapidly replenish the hydrogen sulfide.

By releasing the odor controlling active in a prolonged or delayed manner the effect of the odor controlling active is extended. Specifically, levels of volatile sulfur compounds can be kept considerably lower over a longer period of time.

FIG. 2(a) depicts the controlled release of an odor controlling active from a monolayer film composition as described herein. From FIG. 2(b), it can be readily seen that by releasing an odor controlling agent from the monolayer film of the present invention, the levels of volatile sulfur compounds such as $H_2S$ can be kept at a much lower level for a prolonged or extended period of time.

FIG. 3(a) depicts the controlled release of an odor control active from a multi-layer film composition as described herein. As a result of the controlled release of the odor controlling active from the multi-layer film composition, the level of volatile sulfur compounds is kept at a much lower level for a prolonged or extended period of time. (See, FIG. 3(b)).

In various embodiments, the oral care compositions comprise a plurality of lamellar film fragments entrained in a carrier. In some embodiments, the composition comprises a film, wherein the film comprises lamellar fragments of the film material. In other embodiments, the composition comprises a carrier having distributed therein a plurality of lamellar fragments, wherein the fragments comprise a matrix and a functional odor controlling or odor blocking active compound. In one such embodiment, the composition comprises a film. Such fragments may be of any of a variety of shapes or forms, including semi-solid or solid discrete portions, fragments, particles, flakes, or combinations thereof. In various embodiments, the film comprises a first plurality of fragments and a second plurality of fragments, wherein the first plurality of fragments differ in composition or appearance from the second plurality of fragments. Such difference in composition or appearance can be in any aspect of the composition of the fragment (e.g., different film components, different functional material, different formulation colorant), different appearance (e.g., shape, color, texture, refractive index, reflective index), or combinations thereof.

In various embodiments, the fragments exhibit perceivable contrast with the carrier. The perceivable contrast can be sensory contrast, such as optical contrast, tactile contrast, taste contrast, or olfactory contrast. In some configurations, optical contrast can be color contrast, or a difference in refractive index or reflective index. In some configurations, color contrast can be imparted by one or more colorants that comprise different components of the composition. In various embodiments, the present invention provides compositions comprising a plurality of film fragments in a carrier, wherein said fragments are visibly discernable. As referred to herein, "visibly discernable" refers to one or more characteristics of a fragment which cause the fragment to have a different physical appearance, preferably to the naked eye, relative to the carrier in which the fragment is entrained. Such characteristics include color, opacity, refractive index, reflective index, size, shape, and combinations thereof.

In various embodiments, the fragments have a non-random shape. In one embodiment, a "non-random" shape is a shape which results from a manufacturing process of shaping, cutting, or other forming process by which a specific shape is imparted to a fragment. In such embodiments, a non-random shape is distinguished from such shapes that result from simple precipitation or grinding of a material. In one embodiment, a "non-random" shape is "repeating," wherein the composition comprises a plurality of fragments have substantially the same shape. Such repeating shape may have any of a variety of forms, and may be selected based on a variety of aesthetic or functional criteria. In certain embodiments, the shape of a film fragment can be a recognizable shape. In certain embodiments, a film fragment can comprise a nonrandom shape. Such shapes include simple geometric shapes, such as polygons and elliptical shapes, such as triangles, quadrilaterals (such as a square, a rectangle, a rhombus), pentagons, hexagons, oval, and circles. In one embodiment, the repeating shape is a square. Repeating shapes include, in other embodiments, shapes that are representative of figures or animate or inanimate objects, such as stars, hearts, gems, flowers, trees, shamrocks, a letter of an alphabet, numbers, animals, people, and faces. In various embodiments, the composition comprises a single repeating shape. In other embodiments, the composition comprises a plurality of fragments having a plurality of repeating shapes. In one embodiment, the compositions of the present invention comprise a plurality of first film fragments having a first repeated shape and a plurality of second film fragments having a second repeated shape, wherein the first repeated shape is different from the second repeated shape.

In various embodiments, the size of the fragments is not critical, and may be determined pursuant to any of a variety of criteria, including manufacturing convenience, affect on visual appearance, surface area, affect on texture in the composition, and combinations thereof. In some embodiments, the film fragments can be up to 1 inch (25.4 mm) in length in the longest dimension. As referred to herein, "long dimension" is the dimension of a fragment in length or width (i.e., in the x- and y-dimensions, as the fragment is, or is deformed to be, in a planar shape) in a dimension substantially perpendicular to the "thickness" or shortest dimension of the fragment (i.e., the z-dimension). It is understood that in various embodiments comprising a plurality of fragments, the fragments may be present in a range of sizes due to a variety of factors, including random variation in size, manufacturing tolerances, and intentional sizing or mixing of the fragments through sieving or similar means. As referred to herein, sizes refer to the average size of fragments in a given plurality of fragments.

In various embodiments, the fragments are from 0.2 mm to 15 mm in long dimension. In various embodiments, the long dimension of the fragments is from 0.2 mm to 10 mm, from 0.5 mm to 10 mm, from 0.8 mm to 8 mm, from 0.9 mm to 5 mm, from 1.0 mm to 5 mm, or from 1.5 mm to 2.5 mm. In some embodiments, the long dimension of the fragments is at least 3 mm, and can be from 6 mm to 13 mm. In certain embodiments, a plurality of film fragments is greater than 600 microns in the longest dimension. In certain embodiments, a plurality of film fragments is greater than about 1 millimeter in the longest dimension.

In various embodiments, the fragments of the present invention have a thickness of from 1 mil (thousandth of an inch, 25.4 microns) to 3 mils (76.2 microns). In various embodiments, the fragments have a thickness of less than 4 mils or less than 100 microns and from 0.1 mils (2.54 microns) up to 10 mils (254 microns), from 0.5 mils (12.7 microns) up to 5 mils (127 microns), from 1.4 mils (35.6 microns) to 2.0 mils (50.8 microns).

In some embodiments, the compositions of the present invention comprise fragments having an aspect ratio of at least 5:1. As referred to herein, "aspect ratio" of a fragment is the ratio of the diameter of the smallest imaginary sphere that can enclose the object to the diameter of the largest imaginary sphere that can be completely inside the object and tangent to the surfaces of the object. For example, the aspect ratio of a sphere is 1:1; in another example, the aspect ratio of a cylinder that is 2 inches (50.8 mm) long and ¼ inch (6.35 mm) in diameter is slightly over 8:1; in yet another example, a film fragment of the present invention that is 1 mil (25.4 microns) in thickness, 1 inch (25.4 mm) in length, and 1 inch (25.4 mm) wide has an aspect ratio of about 1414:1.

In some embodiments, the compositions of the present invention comprise fragments having an aspect ratio of at least 10:1. In various embodiments, the fragments have an aspect ratio of from 5:1 to 10,000:1, from 5:1 to 500:1, from 10:1 to 1,000:1, from 10:1 to 100:1, from 20:1 to 100:1, or from 25:1 to 35:1.

In various embodiments, the film comprises a formulation colorant that imparts a color to the film, the composition, or both. In various embodiments, the film fragments contrast with the carrier, and are white, black, or of any color that is visible against or contrasts with the carrier background. Formulation colorants among those useful herein include non-toxic water soluble dyes or pigment, such as, for example, metallic oxide "lakes." In certain embodiments, the colorant is approved for incorporation into a food or drug by a regulatory agency, such as FD&C or D&C pigments and dyes approved by the FDA for use in the United States. Colorants among those useful herein include FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-Δ-3,5-cyclohexadienimine], FD&C Blue No. 1 (disodium salt of dibenzyldiethyl-diaminotriphenylcarbinol trisulfonic acid anhydrite), FD&C Blue No. 2 (sodium salt of disulfonic acid of indigotin), and mixtures thereof in various proportions. In one embodiment, the colorant comprises a water insoluble inorganic pigment, such as titanium dioxide, chromium oxide green, phthalocyanine green, ultramarine blue, ferric oxide, or a water insoluble dye lake. In some embodiments, dye lakes include calcium or aluminum salts of an FD&C dye such as FD&C Green #1 lake, FD&C Blue #2 lake, D&C Red #30 lake or FD&C # Yellow 15 lake. In certain embodiments, a water soluble dye, such as, for example, FD&C Blue #1, is contained within a water-insoluble polymer such as, for example polyethylene such as that found in polyethylene beads (e.g., Microblue Spectra-beads, sold by Micropowders, Inc.). In certain embodiments, the film comprises a dye such as D&C Red #30. In certain embodiments, a white colorant is used, for example titanium dioxide ($TiO_2$), titanium dioxide coated mica (e.g., Timiron), a mineral, or a clay. In certain embodiments, the colorant is a non-bleeding dye. In various embodiments, the film comprises a colorant at a level of from about from 0.5% to 20% by weight of the film, or from 1% to 15% by weight of the film, or from 3% to 12% by weight of the film. In one embodiment, the compositions of the present invention comprise a first plurality of film fragments comprising a first color, and a second plurality of film fragments comprising a second color. Preferably, the second color is different than the first color.

In some embodiments, the film disintegrates during use of the composition. In other embodiments, the film does not disintegrate during use of the composition. In some embodiments, the film releases a material, such as the odor controlling active compound, into the carrier. As referred to herein, "disintegrate" refers to physical disruption of the film or fragment material, so as to produce a film or film fragments of reduced size compared to the original film. Such disruption may be through mechanical, chemical, or physical-chemical means. The disintegration can result, for example, from shearing, grinding, or exposure to elevated temperatures during use. In various dentifrice embodiments of the present invention, such disintegration results from brushing of the composition on the teeth of the subject using the composition. In one embodiment, the film disintegrates so as to release a functional odor controlling active material (as further described herein). In some embodiments, a film fragment can disintegrate into small pieces that are not visually discernable. In some embodiments, the film fragments disintegrate to collectively form a colloid or gel.

In various embodiments, the mono or multilayered films of the present invention may include, in addition to the odor controlling active and without limitation, other functional actives such as:

A. flavorants or flavor components such as menthol, WS3™ that can deliver longer-lasting feeling of fresher or cleaner breath, B. sensate ingredients such as those providing cooling, tingling or heat for example, spilanthol, capsaicin, cinnammic aldehyde C. masking fragrances such as ionones D. bacteriostatic or antibacterial agents such as magnolia bark extract, magnolol, honokiol, triclosan, cetyl pyridinium chloride (CPC), chlorhexidine, and the like E. metal salts of bismuth, copper, zinc, stannous, and the like.

In other embodiments, the film may comprise, without limitation in addition to the odor controlling actives other therapeutic actives. As referred to herein, a therapeutic active is a material that is useful for the prevention or treatment of a physiological disorder or condition. Such disorders or conditions include those of the oral cavity (including the teeth and gingiva), skin, hair, and eyes. The specific therapeutic active is preferably determined according to the desired utility of the composition. Such actives include the following:

A. antimicrobial agents, such as triclosan, cetyl pyridium chloride, domiphen bromide, quaternary ammonium salts, sanguinarine, fluorides, alexidine, octonidine, EDTA, essential oils such as thymol, methyl salicylate, eucalyptol and menthol, and the like, B. non-steroidal anti-inflammatory drugs, such as aspirin, acetaminophen, ibuprofen, ketoprofen, diflunisal, fenoprofen calcium, naproxen, tolmetin sodium, indomethacin, and the like, C. anti-tussives, such as benzonatate, caramiphen edisylate, menthol, dextromethorphan hydrobromide, chlophedianol hydrochloride, and the like, D. decongestants, such as pseudoephedrine hydrochloride, phenylepherine, phenylpropanolamine, pseudoephedrine sulfate, and the like, E. anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like, F. expectorants, such as guaifenesin, ipecac, potassium iodide, terpin hydrate, and the like, G. anti-diarrheals, such a loperamide, and the like, H. $H_2$-antagonists, such as famotidine, ranitidine, and the like; and I. proton pump inhibitors, such as omeprazole, lansoprazole, and the like, J. general nonselective CNS depressants, such as aliphatic alcohols, barbiturates and the like, K. general nonselective CNS stimulants such as caffeine, nicotine, strychnine, picrotoxin, pentylenetetrazol and the like, L. drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like, M. antiparkinsonism drugs such as levodopa, amantadine and the like, N. narcotic-analgesics such as morphine, heroin, hydromorphone, metopon, oxymorphone, levorphanol, codeine, hydrocodone, xycodone, nalorphine, naloxone, naltrexone and the like, O. analgesic-antipyretics such as salycilates, phenylbutazone, indomethacin, phenacetin and the like, P. psychopharmacological drugs such as chlorpromazine, methotrimeprazine, haloperidol, clozapine, reserpine, imipramine, tranylcypromine, phenelzine, lithium and the like. The amount of medicament that can be used in the films of the present invention can be dependent upon the dose needed to provide an effective amount of the medicament.

In various embodiments, therapeutic agents useful herein include anticaries agents, tartar control agents, antiplaque agents, periodontal actives, breath freshening agents, malodour control agents, whitening agents, antibacterials, steroids, anti-inflammatory agents, vitamins, proteins, conditioning agents, moisturizers, antiperspirant actives, deodorant actives, anesthetics, and mixtures thereof.

In certain oral care embodiments, the film or the oral care composition may comprise an oral care active, which is useful for the prevention or treatment of an oral care disorder or condition. Oral care actives among those useful herein include abrasives, anticaries agents, tartar control agents, antiplaque agents, periodontal actives, breath freshening agents, malodour control agents, tooth desensitizers, salivary stimulants, whitening agents, and combinations thereof. Active materials among those useful herein are described in U.S. Pat. No. 6,596,298, Leung et al.

Tartar control agents among those useful herein include dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$; long chain polyphosphates such as sodium hexametaphosphate; and cyclic phosphates such as sodium trimetaphosphate. In some configurations, a polyphosphate is a β-phase calcium pyrophosphate, such as disclosed in U.S. Pat. No. 6,241,974, White, Jr. In some embodiments, the film comprises an anticalculus agent at a level of about 15 to 20% by weight of the film.

Other odor controlling actives useful herein include sulfur precipitating agents. Such sulfur-precipitating agents include metal salts, such as a copper salt or a zinc salt. Such salts include copper gluconate, zinc citrate and zinc gluconate. These zinc salts can be used in combination or in addition to the zinc compounds included in the film. In various embodiments, the film comprises sulfur precipitating agents at a level of from about 0.01 to about 30% by weight of film, from about 2% to about 2.5% by weight of film, or about 10% to about 20% by weight of film.

In a certain embodiments, the film and/or oral composition may include a saliva stimulating agent (a "succulent"). Such agents include those disclosed in U.S. Pat. No. 4,820,506, Kleinberg et al. In some configurations, a saliva stimulating agent can include a food acid such as citric, lactic, malic, succinic, ascorbic, adipic, fumaric and tartaric acids. In various embodiments, the film comprises a saliva stimulating agent at a level of from 0.5 to 70% by weight of the film, from 10% to 50% by weight of the film, or from 30% to 40% by weight of the film. In some embodiments, a saliva stimulating agent can be used in the amelioration of dry mouth.

In certain oral care embodiments, the film comprises other active materials, such as antibacterial agents such as magnolia extract, triclosan, grapeseed extract, thymol, methyl salicylate, eucalyptol, menthol, hop acids, cetyl pyridinium chloride, (including CPC/Zn and CPC+enzymes) and usnic acid; anti-inflammatory agents such a breath freshening agents (for example zinc gluconate, zinc citrate, zinc chlorite and alpha ionone); tooth desensitizers such as potassium nitrate, desensitizing polymers, and desensitizing minerals; anti-inflammatory agents such as magnolia extract, ursolic acid; aloe, and cranberry extract; vitamins such as pantheon, retinyl palmitate, folic acid, tocopherol acetate and Vitamin A; herbs or herbal extracts such as rosemary, oregano, chamomilla recutita, *mentha piperita, salvia officinalis*, orcommiphora and myrrha; proteins, such as milk proteins and enzymes such as peroxide-producing enzymes, amylase, plaque disrupting agents such as papain, glucoamylase, and glucose oxidase; whitening agents such as hydrogen peroxide, urea peroxide and phosphate salts; medicinals, such as aspirin (acetyl salicylic acid), caffeine, and benzocaine; probiotics; abrasives such as silicas (including high cleaning silica); anti-caries agents such as stannous salts (e.g., stannous fluoride) or amino fluoride; a nitric oxide synthase inhibitor such as guanidinoethyldisulfide; calcium; antiattachment ingredients, such as polyvynylphosphonic acid; silicones; chlorophyll compounds, anti-leukoplakia agents such as beta-carotene; anti-oxidants such as Vitamin E; and combinations thereof. In some embodiments, the films comprise such active materials at a concentration of about 0.01 to about 30% by weight of film, from about 2% to about 25% by weight of the film, or from about 10% to about 20% by weight of film.

In certain embodiments, the film and/or oral care composition includes a preservative. A preservative can be added in amounts from about 0.001 w/w % to about 5 w/w %, preferably from about 0.01 w/w % to about 1 w/w % of the film. Non-limiting examples of preservatives include sodium benzoate and potassium sorbate.

Some embodiments of present invention provide a composition comprising a carrier in which a film, or one or more film fragments, is entrained. As referred to herein, a "carrier" is any material or composition in which a film can be entrained and is suitable for administration or application to the human or animal subject to whom the composition is administered or applied.

As referred to herein, "entrained" refers to the embedding, dispersing or suspending or other distribution of a film in a carrier. In various embodiments comprising a plurality of fragments, such fragments may be entrained by embedding, suspension, dispersion or other distribution of the fragments in the carrier. In various embodiments, the fragments are distributed substantially homogenously throughout the carrier. In other embodiments, the fragments are not distributed homogenously in the carrier. In certain embodiments, the distribution of a plurality of film fragments is substantially isotropic within the carrier. Dentifrice compositions that include a plurality of film fragments dispersed or suspended in a carrier are commercially available under the tradename Max Fresh® or Max White®, from Colgate-Palmolive Company, New York, N.Y.

Some embodiments comprise two phases, wherein one phase comprises a carrier and a second phase comprises the aforementioned film or fragment. The term "phase" as used herein denotes a physical phase as understood in the physical and material sciences, i.e., a portion of a material whose properties and composition are uniform. However, a phase as used herein can be discontinuous, i.e., a phase can comprise a plurality of separate components. For example, a plurality of polymer film fragments of identical composition is considered to comprise a single phase. In some embodiments, a film fragment can be entirely embedded within the material comprising the first phase, or totally or partially exposed on the surface of the first phase. For example, if the composition is a dentifrice comprising both a gel and film fragments, a film fragment can be totally surrounded by the gel, or partially or totally exposed on the surface of the gel. In certain embodiments, compositions comprise more than two phases. Such multi-phase compositions include those having two carriers, each of which contributes a phase to the composition, in addition to film fragments as described herein. Other multi-phase compositions include those having a single carrier and two or more pluralities of fragments, wherein the pluralities of fragments have differing compositions.

In various embodiments, the carrier is a liquid, semi-solid or solid. A "liquid" can be a liquid of low or high viscosity. A liquid can be a liquid such that flow is imperceptible under ambient conditions. For example, a soap, such as an ordinary bar of hand soap, can be considered a liquid herein. A liquid can be a thixotropic liquid. A "semi-solid" as used herein can be a gel, a colloid, or a gum. As used herein, semi-solids and liquids are fluids distinguished on the basis of viscosity: a semi-solid is a high viscosity fluid, while a liquid has lower viscosity. There is no definitive dividing line between these two types of fluids. A semi-solid can, in certain embodiments, have a viscosity as high as thousands of mPa·s. Carriers among those useful herein include liquids, pastes, ointments, and gels, and can be transparent, translucent or opaque.

In certain embodiments, the compositions of the present invention are oral care compositions, suitable for administration to the oral cavity. Such compositions include dentifrices, mouthwashes, dental gels, lozenges, beads, gums, oral strips, mints, liquid toothpastes, sprays, paint-on gels, lip balms, whitening strips, breath strips, oral chews, and combinations thereof. An oral care composition disclosed herein can be used, for example, for cavity prevention, whitening, plaque prevention or reduction, gingivitis prevention or reduction, tartar control, sensitivity prevention or reduction, or breath malodor prevention or reduction, and stain prevention.

The specific composition of the carrier preferably depends on the intended use of the composition. In various embodiments, the carrier is aqueous, comprising from 5% to 95% water or from 10% to 70% water. In other embodiments, the carrier is substantially non-aqueous. In a dentifrice carrier, water content can be from 5% to 70%, from 10% to 50%, or from 20% to 40%. When the presence of water will cause the film to disintegrate, it is particularly preferred that the dried film contain no free water, in which the amount of water is substantially 0%, or negligible.

The carrier may comprise any of a variety of materials, including emulsifiers, thickeners, fillers, and preservatives. In some embodiments, the carrier may include a functional or active material, such as those described above. In some embodiments, the carrier comprises the same functional material as the film.

In some embodiments, the carrier is suitable for use as a dentifrice. In other embodiments, the carrier comprises a humectant, such as glycerine, sorbitol or an alkylene glycol such as polyethylene glycol or propylene glycol. In some embodiments, the carrier comprises a humectant at a level of from 10% to 80% by weight, or 20% to 60% by weight of the composition. Carrier compositions among those useful herein are disclosed in U.S. Pat. No. 5,695,746, Garlick, Jr., et al, and U.S. Pat. No. 4,839,157, Mei-King Ng et al.

In various dentifrice embodiments, the carrier comprises thickeners, gelling agents or combinations thereof. Thickeners or gelling agents useful herein include inorganic, natural or synthetic thickeners or gelling agents. In some configurations, the carrier comprises the thickener and gelling agent at total levels of from 0.10% to 15% by weight, or from 0.4% to 10% by weight of the composition. Examples of thickeners and gelling agents useful herein include inorganic thickening silicas such as: an amorphous silica, for example Zeodent® 165 (Huber Corporation); Irish moss; iota-carrageenan; gum tragacanth; or polyvinylpyrrolidone. In certain embodiments, the carrier comprises a polishing agent, such as a silica, a calcined alumina, sodium bicarbonate, calcium carbonate, dicalcium phosphate or calcium pyrophosphate. In various embodiments, the carrier can be a visually clear composition.

In various dentifrice embodiments, comprising a visually clear carrier, the composition comprises at least one polishing agent. Polishing agents among those useful herein include collodial silica, such as, for example, Zeodent® 115 (Huber Corporation), and alkali metal aluminosilicate complexes (i.e., a silica comprising alumina). In some configurations, a polishing agent can have a refractive index close to that of a gelling agent combined with water and/or humectant. In various embodiments, the carrier comprises the polishing agent at a level of from 5% to 70% by weight of the composition.

In certain dentifrices, the carrier comprises a surfactant or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate; and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments the carrier comprises the surfactant at a level of from about 0.3% to about 5% by weight of composition, or 0.5% to 3% by weight of composition.

The present invention also provides methods for making a dentifrice carrier. In one embodiment, water and at least one humectant are dispersed in a conventional mixer until a first homogeneous gel phase is formed. A polishing agent is then added into the first homogeneous gel phase. The first homogeneous gel phase and the polishing agent are mixed until a second homogeneous gel phase is formed. A thickener, flavorant and surfactants are added to the second homogeneous gel phase. These ingredients are mixed at high speed under vacuum of 20 to 100 mmHg.

The compositions of the present invention are preferably stable under normal conditions of storage. As referred to herein, "stable" refers to the lack of significant adverse effect on one, and preferably all, compositional attributes such as appearance, flavor, rheology, and chemical composition of the composition. Preferably, stability in the present compositions includes the compositional and physical stability of film (including fragments, if any) in the composition. In various embodiments a composition comprising a film is stable upon storage at ambient temperature for at least about two years. It is understood, however, that in some embodiments, an otherwise stable film can disintegrate during use (as discussed above), for example, during toothbrushing using a dentifrice composition.

In certain embodiments, a composition can comprise, in addition to film fragments as described herein, two or more carriers, each of which contributes a phase to the composition. Such a composition can be stable to color bleeding. For example, a composition can include film fragments and a striped dentifrice such as that disclosed in U.S. Pat. No. 6,315,986, Wong et al. In certain embodiments, the film fragments can be of different color(s) than the stripe(s) for enhanced aesthetic appeal.

The dentifrice composition conventionally includes thickening agents that provide the dentifrice with the required rheological properties, so that the dentifrice can be stored in a dispensing container over a period of time and thereafter reliably dispensed therefrom by the user. The dentifrice preferably should have the correct viscosity not only to be dispensed but also to exhibit an acceptable consistency within the mouth during tooth brushing. Typical thickening agents include modified celluloses, such as carboxymethyl cellulose (CMC), and other polysaccharide or gum components.

The polysaccharide thickening agent may comprise at least one of xanthan gum and hydroxyethyl cellulose. The polysaccharide thickening agent typically consists of at least one of xanthan gum and hydroxyethyl cellulose. Preferably, the polysaccharide thickening agent consists of xanthan gum which is present in an amount of from 0.1 to 1.5 wt % based on the weight of the composition, preferably from 0.5 to 1 wt % of the composition. However, minor amounts of additional thickeners may be present, for example carrageenan, gum tragacanth, starch, polyvinylpyrrolidone, hydroxyethypropyl cellulose, hydroxybutyl methyl cellulose, hydroxypropyl methylcellulose, hydroxyethyl cellulose, sodium carboxymethyl cellulose (sodium CMC) and colloidal silica. In one embodiment, the thickener concentration ranges of 0.1 wt. % to 5 wt. % based on the weight of the composition. In another embodiment, the thickener concentration ranges of 0.5 wt. % to 2 wt. % based on the weight of the composition.

Some embodiments of the present invention also provide processes for preparing compositions comprising a film entrained in a carrier. In various embodiments, a plurality of fragments of the film matrix is combined with a carrier. In some embodiments, a carrier and a plurality of film fragments can be mixed. In some embodiments, the mixing can comprise slow stirring. In other embodiments, the process for preparing the composition comprising a carrier having distributed therein a plurality of lamellar fragments of the films of the present invention comprises: providing the orally acceptable carrier; adding lamellar fragments of the mono or multilayer film for extended or delayed release of an odor controlling active to the orally acceptable carrier to form a mixture; and homogenizing the mixture.

The term "homogenizing" as used herein refers to the admixture of the fragments and the carrier so as to attain a substantially homogeneous distribution of fragments in the carrier. It should be noted, however, that the resulting composition still retains two-phase composition characteristics. Homogenizing may be accomplished using any of a variety of conventional homogenizers.

In some embodiments, the film is added to a component of the orally acceptable carrier (e.g., to a humectant for a dentifrice). The remainder of the carrier then may be made, and the mixture of film then added to the carrier.

Certain embodiments described herein also provide methods for administering an odor controlling active to a human or animal subject. As referred to herein, "administering" refers to any method by which a composition is applied on or administered to the subject. In various embodiments, the administration is topical, wherein the composition is applied to an external surface of the subject, such as to a surface of the oral cavity (e.g., teeth, gingival, and tongue. The specific route and method of administration will depend, of course, on the intended use of the composition.

In some embodiments, the present invention provides methods for administering an odor controlling active to a human or animal subject in need thereof, comprising topically applying to the subject a composition comprising a controlled release film matrix containing an odor controlling active, entrained in a carrier. In some embodiments, the method further comprises disrupting the film matrix after topical application of the composition. In some embodiments, such disruption is accomplished by any of a variety of methods, including chemical and/or mechanical means. Chemical means include degradation of the film by contact with water or a material present at the site of administration (e.g., saliva in an oral care application). Physical means include agitation, grinding, and shear forces produced by application of physical energy to the composition during use (e.g., brushing in a dentifrice application).

In various embodiments, the present invention provides methods for the treatment of a disease or condition of the oral cavity. As used herein, an "oral care condition" refers to a disorder or condition which can be prevented or treated by administration of a composition to the oral cavity, including disorders or conditions of the teeth, oral mucosa, gingiva and tongue. Such conditions include caries, gingivitis, periodontitis, and cosmetic conditions such as yellowing and malodour.

The invention will be described in greater detail by way of specific examples. The following examples are offered for illustrative purposes and are not intended to limit the scope of the invention in any manner. Those of skill in the art will readily recognize a variety of non-critical parameters which can be changed or modified to yield essentially the same results.

EXAMPLES

Example 1

This example illustrates a single layer film containing combinations of Carbopol® CP971 as the adhesive polymer, polyvinyl acetate as the release modulating polymer, hydroxyl propyl methyl cellulose ("HPMC") as the polymeric base and zinc oxide as the odor controlling active as shown in Table 1 below.

TABLE 1

| Ingredient | Film Slurry wt % | Dry Film wt % |
|---|---|---|
| Water | 50.8 | |
| Methocel E5 (HPMC) | 7.2 | 24.6 |
| Methocel E50 (HPMC) | 1.5 | 5.1 |
| Kollicoat ® 30D (27% Polyvinyl acetate, PVA) | 27.3 | 25.2 (as PVA) |
| Carbopol 971 | 1.2 | 4.1 |
| Zinc Oxide | 10.0 | 34.1 |
| Propylene Glycol | 1.5 | 5.1 |

TABLE 1-continued

| Ingredient | Film Slurry wt % | Dry Film wt % |
|---|---|---|
| Tween 80 | 0.5 | 1.8 |
| Total | 100 | 100 |

Example 2

This example illustrates a single layer film containing combinations of Carbopol® CP971 as the adhesive polymer polyvinyl acetate, polyvinyl acetate as the release modulating polymer, HPMC as the polymeric base and Ordenone® as the odor controlling active as shown in Table 2 below.

TABLE 2

| Ingredient | Film Slurry wt % | Dry Film wt % |
|---|---|---|
| Water | 50 | |
| Methocel E5 (HPMC) | 7.2 | 23.9 |
| Methocel E50 (HPMC) | 1.5 | 5.1 |
| Kollicoat ® 30D (27% Polyvinyl acetate, PVA) | 27.3 | 24.5 (as PVA) |
| Carbopol 971 | 1.2 | 4.0 |
| Titanium Dioxide | 0.8 | 2.6 |
| Ordenone | 10 | 33.1 |
| Propylene Glycol | 1.5 | 5.1 |
| Tween 80 | 0.5 | 1.7 |
| Total | 100 | 100 |

Other embodiments could comprise a two-layer film system in which the bottom film layer contain combinations of adhesive polymers, polymeric base and control odor actives or combinations of actives and flavorants. The top layer could contain polyvinyl acetate as the release modulator and combinations of polymeric bases and/or flavorants. Examples 3 and 4 shown below illustrate two-layer polymer film embodiments.

Example 3

This example illustrates a dual layer film containing combinations of carbolpol CP971 as the adhesive polymer, polyvinyl acetate as the release modulator, HPMC as the polymeric base and zinc oxide and/or zinc zeolites, such as those described in U.S. Patent Application No. 2006/0045860, as the bacteriostatic or bacteriocidal active. The dual film formulation includes an adhesive bottom layer with Carbopol® CP971 as the adhesive polymer, HPMC as the polymeric base and a baceriostatic agent such as zinc oxide and/or zinc zeolite as shown in Table 3A below.

TABLE 3A

| Ingredient | Film Slurry wt % | Dry Film wt % |
|---|---|---|
| Water | 73.3 | |
| Methocel E5 (HPMC) | 11.8 | 40 |
| Carbopol 971 | 1.2 | 4 |
| Corn Starch | 2.7 | 10 |
| Zinc Oxide/Zinc Zeolite | 10 | 37 |
| Propylene Glycol | 0.6 | 2 |
| Tween 80 | 0.4 | 1.5 |
| Total | 100 | 100 |

The dual film formulation also includes a slow dissolving top layer having polyvinyl acetate as the release modulator polymer, HPMC as the polymeric base and a flavorant as shown in Table 3B below.

TABLE 3B

| Ingredient | Film Slurry wt % | Dry Film wt % |
|---|---|---|
| Water | 53.4 | |
| Methocel E5 (HPMC) | 7.2 | 27.0 |
| Methocel E50 (HPMC) | 1.5 | 5.7 |
| Kollicoat ® 30D (27% Polyvinyl acetate, PVA) | 27.3 | 27.6 (as PVA) |
| Corn Starch | 2.7 | 10.1 |
| Propylene Glycol | 1.4 | 5.2 |
| Flavorant | 6.0 | 22.5 |
| Tween 80 | 0.5 | 1.9 |
| Total | 100 | 100 |

Example 4

This example illustrates a dual layer film containing combinations of Carbopol® CP971 as the adhesive polymer, polyvinyl acetate as the release modulator, HPMC as the polymeric base and Ordenone® as the odor control active. The dual film formulation includes an adhesive bottom layer with Carbopol® CP971 as the adhesive polymer, HPMC as the polymeric base and Ordenone® as the odor control compound as shown in Table 4A.

TABLE 4A

| Ingredient | Film Slurry wt % | Dry Film wt % |
|---|---|---|
| Water | 73.3 | |
| Methocel E5 (HPMC) | 11.8 | 40 |
| Carbopol 971 | 1.2 | 4 |
| Corn Starch | 2.7 | 10 |
| Ordenone | 10 | 37 |
| Propylene Glycol | 0.6 | 2 |
| Tween 80 | 0.4 | 1.5 |
| Total | 100 | 100 |

The dual film formulation also includes a slow dissolving top layer having polyvinyl acetate as the release modulating polymer, HPMC as the polymeric base and a flavorant as shown in Table 4B below.

TABLE 4B

| Ingredient | Film Slurry wt % | Dry Film wt % |
|---|---|---|
| Water | 53.4 | |
| Methocel E5 (HPMC) | 7.2 | 27.0 |
| Methocel E50 (HPMC) | 1.5 | 5.7 |
| Kollicoat ® 30D (27% Polyvinyl acetate, PVA) | 27.3 | 27.6 (as PVA) |
| Corn Starch | 2.7 | 10.1 |
| Flavorant | 6 | 22.5 |
| Propylene Glycol | 1.4 | 5.2 |
| Tween 80 | 0.5 | 1.9 |
| Total | 100 | 100 |

Example 5

This example illustrates a three layer film having a flavorant containing central layer sandwiched between two surface layers that are fully saliva erodible. Table 5 below sets forth slurry compositions utilized in preparing a three layer film of the present invention.

TABLE 5

| Ingredient | Film Slurry wt % |
|---|---|
| Surface Layer 1 | |
| Water | 84.8 |
| HPMC E5 | 7.2 |
| HPMC E50 | 1.5 |
| Corn Starch | 2.7 |
| Carbopol 971P | 1.2 |
| Titanium Dioxide | 0.7 |
| Propylene Glycol | 1.4 |
| Tween 80 | 0.5 |
| Center Layer 2 | |
| Water | 67.5 |
| HPMC E5 | 12.3 |
| Zinc zeolite | 10 |
| Corn Starch | 2.2 |
| Sucralase Sweetener | 1 |
| Propylene Glycol | 0.6 |
| Flavorant | 6 |
| Tween 80 | 0.4 |
| Surface Layer 3 | |
| Water | 84.8 |
| HPMC E5 | 7.2 |
| HPMC E50 | 1.5 |
| Corn Starch | 2.7 |
| Carbopol 971P | 1.2 |
| Titanium Dioxide | 0.7 |
| Propylene Glycol | 1.4 |
| Tween 80 | 0.5 |

Layer 1 was cast at 5 mils then dried in a 95° C. oven for 15 minutes. Layer 2 was cast over layer 1 at 15 mils then dried in the same manner. Layer 3 was cast at 5 mils and the final composition dried at 95° C. for another 15 minutes. The thickness of dried film is about 2.75 mils with 1.65 mils center flavored layer and 0.55 mils two surface layers. The film is ground into small pieces by using IKA-WERKE (MF 10 basic) in lab. The chips of size between 12 and 20 mesh are collected for making products.

Each patent, patent application, and printed publication, mentioned in this patent document is hereby incorporated by reference in its entirety.

As those skilled in the art will appreciate, numerous changes and modifications may be made to the embodiments described herein, without departing from the spirit of the invention. It is intended that all such variations fall within the scope of the claimed invention.

The invention claimed is:
1. An oral care composition comprising
    an orally acceptable carrier, and
    a multilayer film, wherein
        the multilayer film is entrained in the orally acceptable carrier, and wherein said multilayer film comprises at least one mucoadhesive layer and one overlying layer, and
    wherein the mucoadhesive layer comprises:
        a mucoadhesive polymer,
        a first polymeric base, and
        an odor controlling active; and
    wherein the overlying layer comprises:
        a release modulating polymer,
        a second polymeric base, and
    optionally a flavorant;
        wherein said odor controlling active is a zinc containing compound selected from the group consisting of: zinc oxide; zinc citrate; zinc lactate; zinc chlorite; zinc chloride; zinc zeolite; and a combination of two or more thereof;

wherein the mucoadhesive polymer is selected from the group consisting of a polyacrylic acid or polyacrylate, a cross-linked polyacrylic acid or polyacrylate, a polyalkyl acrylate, a cross-linked polyalkyl acrylate, polyvinylpyrrolidone, a copolymer of polyvinylpyrrolidone and polyacrylate, chitosan or a chemically-modified chitosan, and a combination of two or more thereof;

wherein the release modulating polymer is polyvinyl acetate or hydroxyl ethyl cellulose;

wherein either or both of the first polymeric base and second polymeric base is selected from the group consisting of: hydroxypropylmethyl cellulose; methyl cellulose; hydroxypropyl cellulose; and copolymers thereof;

wherein the mucoadhesive polymer comprises from 2% to 5% by weight of the mucoadhesive layer; and wherein the multilayer film comprises from 0.1% to 5% by weight of the oral care composition.

2. The composition of claim 1, wherein the release modulating polymer comprises from 20% to 30% by weight of the overlying layer.

3. The composition of claim 1, wherein the first polymeric base comprises from 25% to 50% by weight of the multilayer film.

4. The composition of claim 1, wherein the second polymeric base comprises from 25% to 50% by weight of the multilayer film.

5. The composition of claim 1, wherein the odor controlling active comprises from 30% to 40% by weight of the mucoadhesive layer.

6. A method for treating or preventing oral malodor comprising: administering to a subject in need thereof, a controlled release oral care composition according to claim 1.

7. An oral care composition comprising
an orally acceptable carrier, and
a multilayer film, wherein
the multilayer film is entrained in the orally acceptable carrier, and wherein said multilayer film comprises at least one mucoadhesive layer and one overlying layer, and
wherein the mucoadhesive layer comprises:
a mucoadhesive polymer,
a first polymeric base, and
an odor controlling active; and
wherein the overlying layer comprises:
a release modulating polymer,
a second polymeric base, and
optionally a flavorant;

wherein said odor controlling active is a zinc containing compound selected from the group consisting of: zinc oxide; zinc citrate; zinc lactate; zinc chlorite; zinc chloride; zinc zeolite; and a combination of two or more thereof;

wherein the mucoadhesive polymer is selected from the group consisting of a polyacrylic acid or polyacrylate, a cross-linked polyacrylic acid or polyacrylate, a polyalkyl acrylate, a cross-linked polyalkyl acrylate, polyvinylpyrrolidone, a copolymer of polyvinylpyrrolidone and polyacrylate, chitosan or a chemically-modified chitosan, and a combination of two or more thereof;

wherein the release modulating polymer is polyvinyl acetate or hydroxyl ethyl cellulose;

wherein either or both of the first polymeric base and second polymeric base is selected from the group consisting of: hydroxypropylmethyl cellulose; methyl cellulose; hydroxypropyl cellulose; and copolymers thereof;

wherein the mucoadhesive polymer comprises from 2% to 5% by weight of the mucoadhesive layer;

wherein the release modulating polymer comprises from 20% to 30% by weight of the overlying layer;

wherein the first polymeric base comprises from 25% to 50% by weight of the multilayer film;

wherein the second polymeric base comprises from 25% to 50% by weight of the multilayer film;

wherein the odor controlling active comprises from 30% to 40% by weight of the mucoadhesive layer; and wherein the multilayer film comprises from 0.1% to 5% by weight of the oral care composition.

8. The composition of claim 1, wherein the composition comprises two phases, wherein one phase comprises the orally acceptable carrier and the second phase comprises the multilayer film.

* * * * *